United States Patent
Osborne et al.

(10) Patent No.: US 8,608,761 B2
(45) Date of Patent: Dec. 17, 2013

(54) THROMBUS REMOVAL DEVICE

(75) Inventors: Thomas A. Osborne, Bloomington, IN (US); Shyam Kuppurathanam, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/553,041

(22) Filed: Jul. 19, 2012

(65) Prior Publication Data

US 2013/0018410 A1 Jan. 17, 2013

Related U.S. Application Data

(62) Division of application No. 11/936,525, filed on Nov. 7, 2007, now Pat. No. 8,246,641.

(60) Provisional application No. 60/857,760, filed on Nov. 8, 2006.

(51) Int. Cl.
*A61B 17/22* (2006.01)
*A61D 1/02* (2006.01)

(52) U.S. Cl.
USPC .......................................................... 606/159

(58) Field of Classification Search
USPC ......... 606/110, 113, 114, 127, 128, 159, 200; 604/22
See application file for complete search history.

(56) References Cited

U.S. PATENT DOCUMENTS

| | | |
|---|---|---|
| 3,683,891 A | 8/1972 | Eskridge et al. |
| 3,749,085 A | 7/1973 | Willson et al. |
| 4,030,503 A | 6/1977 | Clark, III |
| 4,706,671 A | 11/1987 | Weinrib |
| 4,886,490 A | 12/1989 | Shiber |
| 5,011,488 A | 4/1991 | Ginsburg |
| 5,192,268 A | 3/1993 | Shiber |
| 5,269,751 A | 12/1993 | Kaliman et al. |
| 5,284,486 A | 2/1994 | Kotula et al. |
| 5,893,869 A | 4/1999 | Barnhart et al. |
| 5,895,398 A | 4/1999 | Wensel et al. |
| 5,980,514 A | 11/1999 | Kupiecki et al. |
| 6,063,069 A | 5/2000 | Cragg et al. |
| 6,066,158 A | 5/2000 | Engelson et al. |
| 6,436,112 B2 | 8/2002 | Wensel et al. |

(Continued)

OTHER PUBLICATIONS

Notice of Allowance from related U.S. Appl. No. 11/502,659 dated Oct. 21, 2011 (7 pgs).
Non-Final Office Action from related U.S. Appl. No. 11/502,659 dated Jun. 7, 2011 (8 pgs).
Non-Final Office Action from related U.S. Appl. No. 11/502,659 dated Dec. 20, 2010 (9 pgs).

(Continued)

*Primary Examiner* — Ryan Severson
*Assistant Examiner* — Katherine M Shi
(74) *Attorney, Agent, or Firm* — Brinks Gilson & Lione

(57) ABSTRACT

A thrombus removal device includes a shaft with a distal end and a proximal end, a sheath with a distal end and a proximal end, and a helical coil attached at a proximal end to the distal end of the shaft and is disposed within the lumen of the sheath in a closed configuration. The helical coil includes a plurality of body portions with turns spaced apart longitudinally and laterally to facilitate screwing the helical coil into a thrombus and also providing an open area into which the thrombus can be captured. A distal tip of the helical coil is provided with a loop, an angle of which is about the same as the angle of at least one body portion. The helical coil assumes an open configuration when the sheath is retracted proximally from the distal tip.

4 Claims, 7 Drawing Sheets

(56) References Cited

U.S. PATENT DOCUMENTS

| | | | |
|---|---|---|---|
| 6,454,775 | B1 | 9/2002 | Demarais et al. |
| 6,485,497 | B2 | 11/2002 | Wensel et al. |
| 6,530,935 | B2 | 3/2003 | Wensel et al. |
| 6,663,650 | B2 | 12/2003 | Sepetka et al. |
| 6,692,508 | B2 | 2/2004 | Wensel et al. |
| 6,692,509 | B2 | 2/2004 | Wensel et al. |
| 6,730,104 | B1 | 5/2004 | Sepetka et al. |
| 2002/0123765 | A1* | 9/2002 | Sepetka et al. ............ 606/192 |
| 2006/0064114 | A1 | 3/2006 | Obitsu et al. |
| 2006/0074409 | A1 | 4/2006 | Schuermann |
| 2006/0195137 | A1* | 8/2006 | Sepetka et al. ............ 606/200 |

OTHER PUBLICATIONS

Advisory Action from related U.S. Appl. No. 11/502,659 dated Aug. 16, 2010 (3 pgs).

Final Office Action from related U.S. Appl. No. 11/502,659 dated Jun. 3, 2010 (11 pgs).

Non-Final Office Action from related U.S. Appl. No. 11/502,659 dated Dec. 30, 2009 (9 pgs).

Advisory Action from related U.S. Appl. No. 11/502,659 dated Sep. 2, 2009 (3 pgs).

Final Office Action from related U.S. Appl. No. 11/502,659 dated Jun. 12, 2009 (7 pgs).

Non-Final Office Action from related U.S. Appl. No. 11/502,659 dated Nov. 12, 2008 (8 pgs).

* cited by examiner

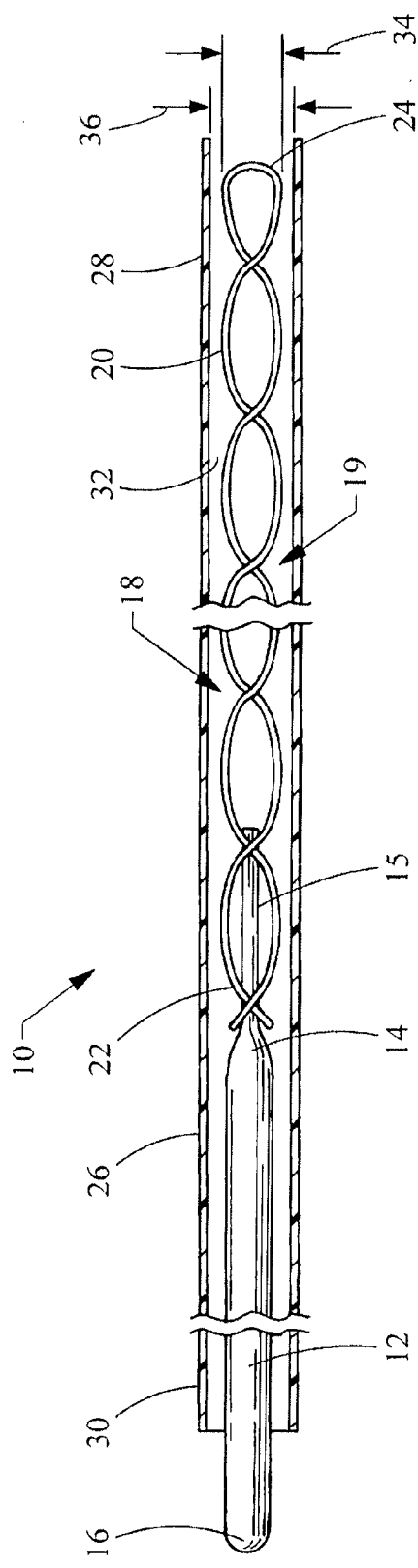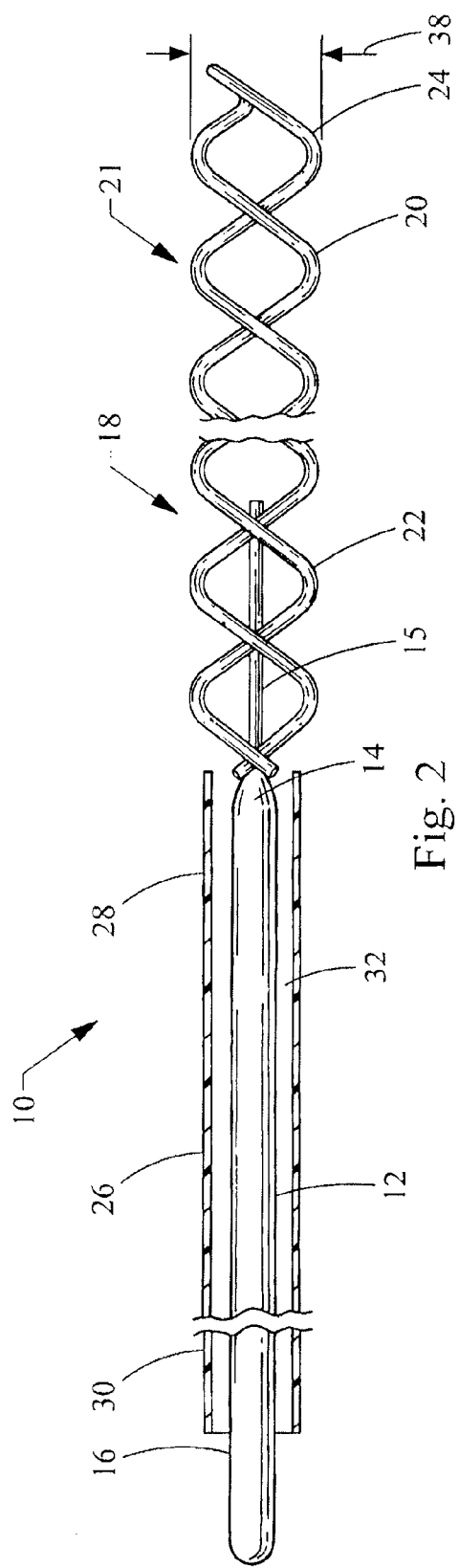

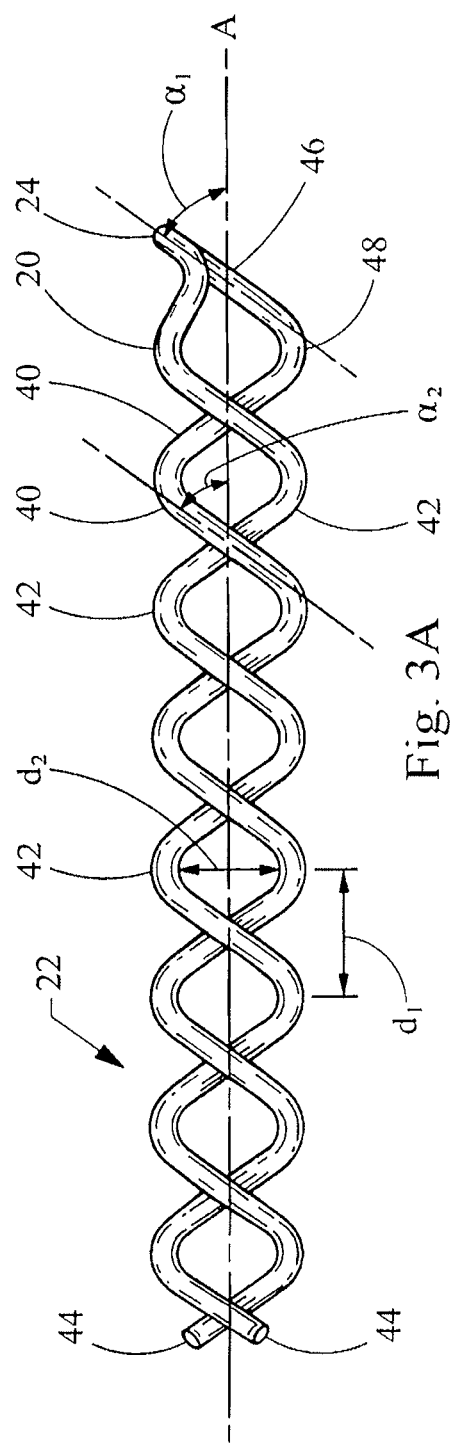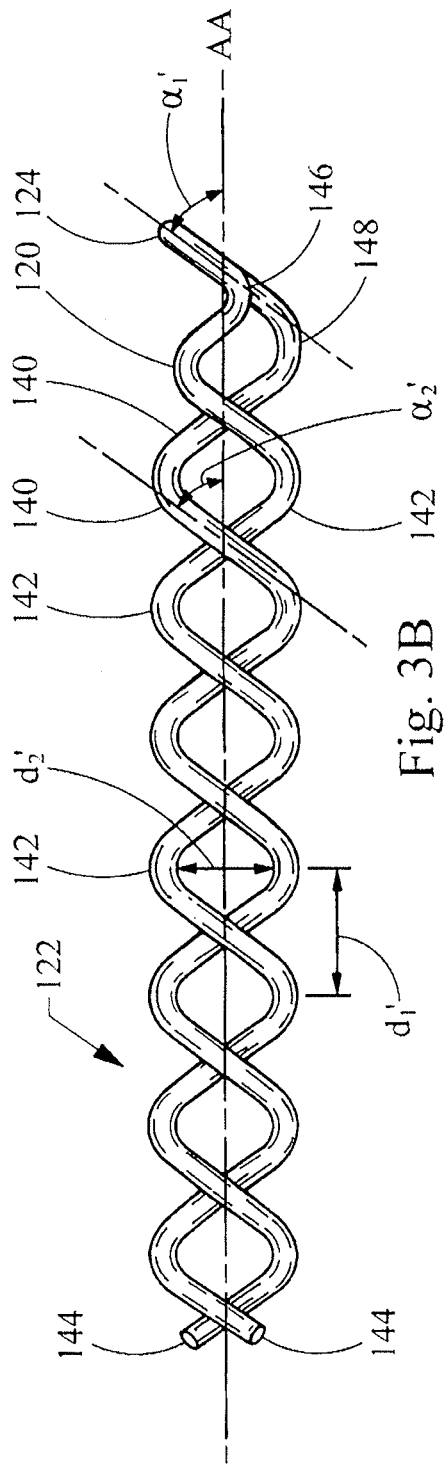
Fig. 3A
Fig. 3B

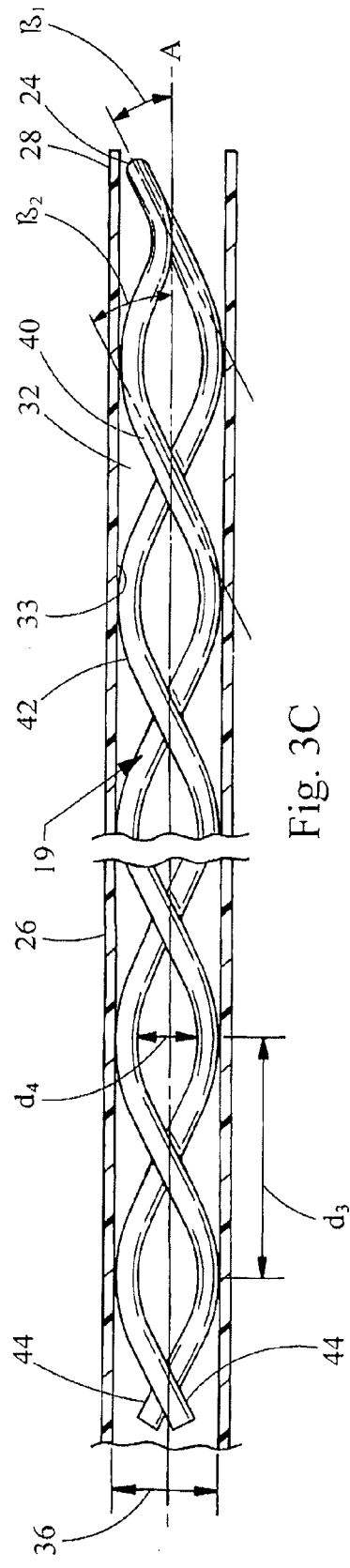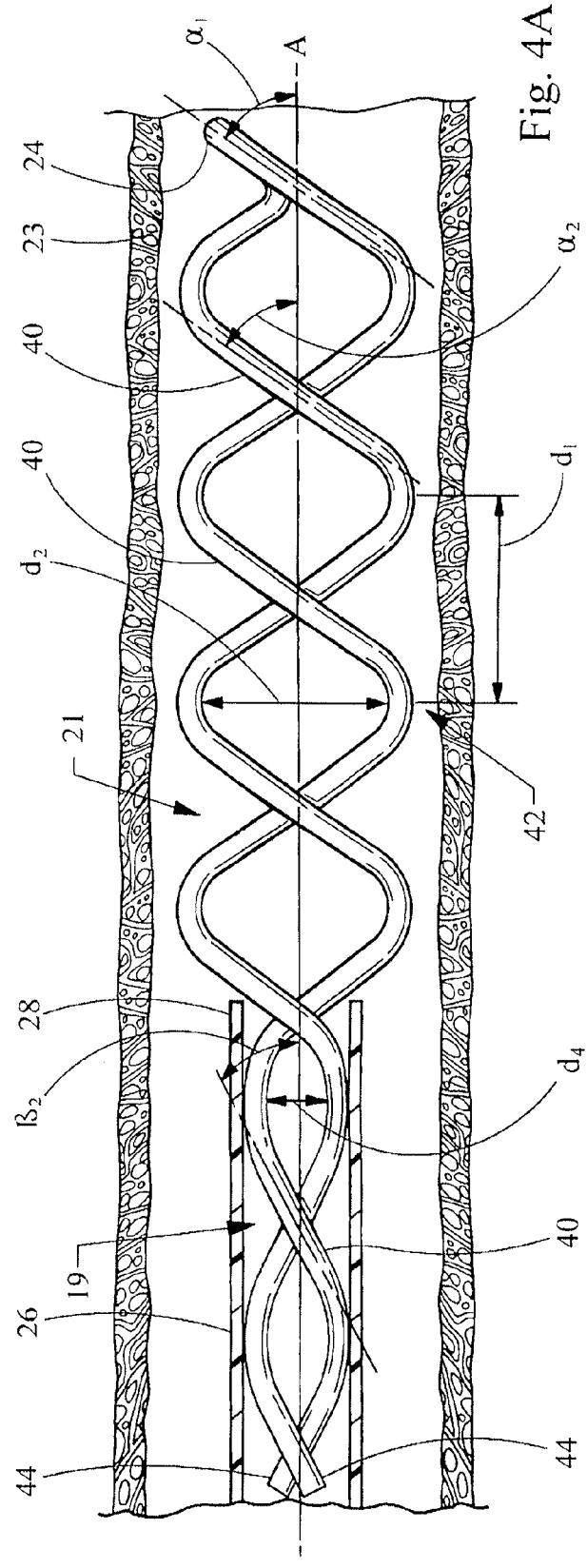
Fig. 3C
Fig. 4A

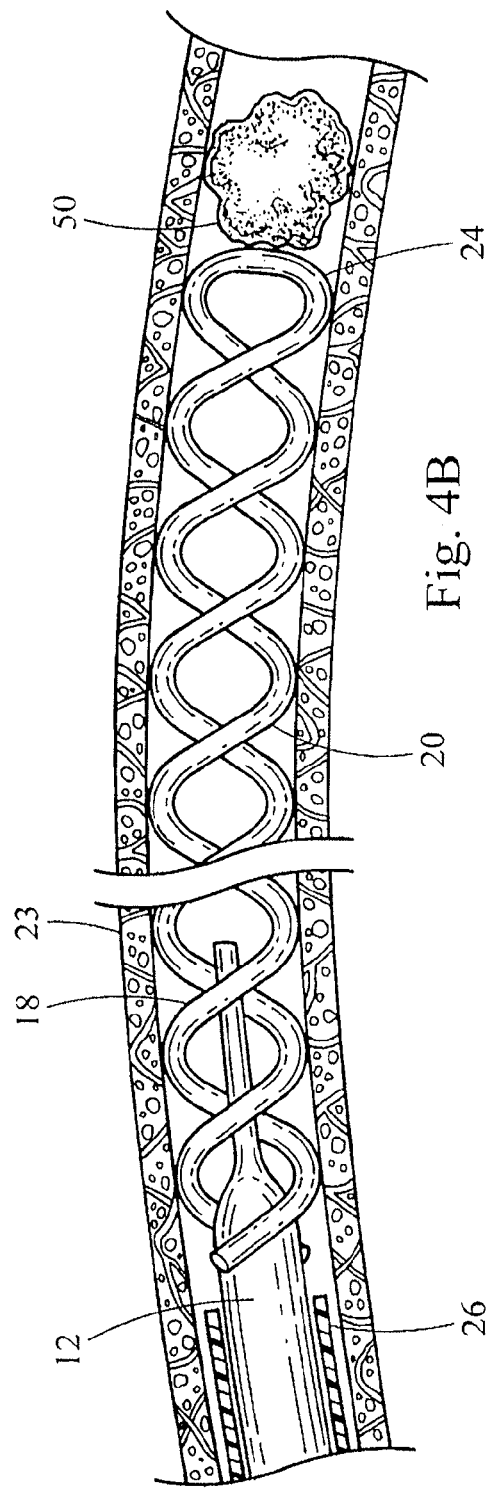
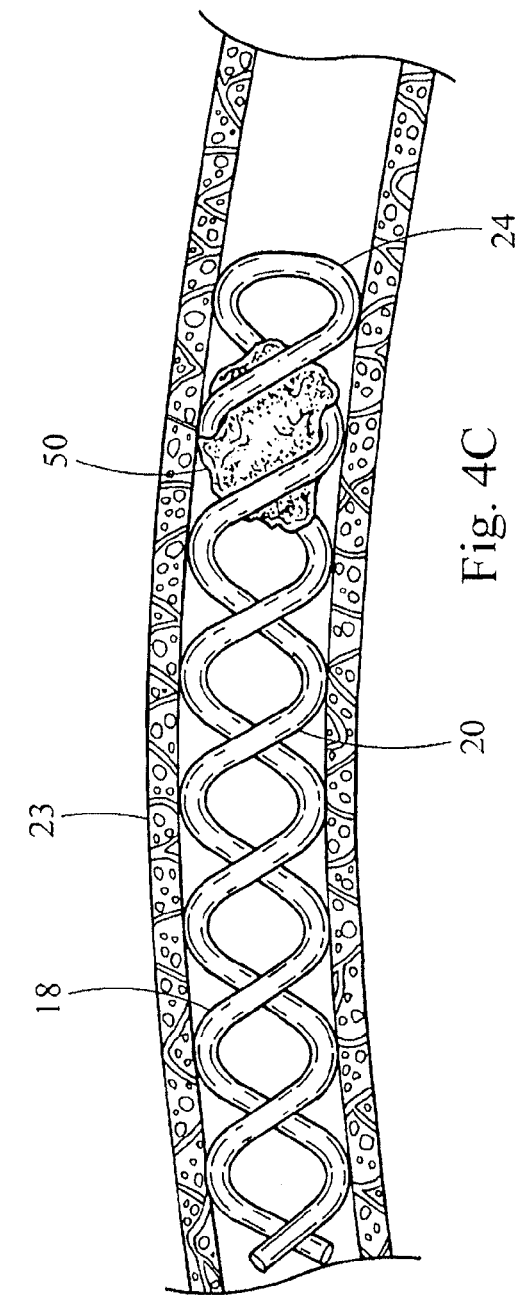

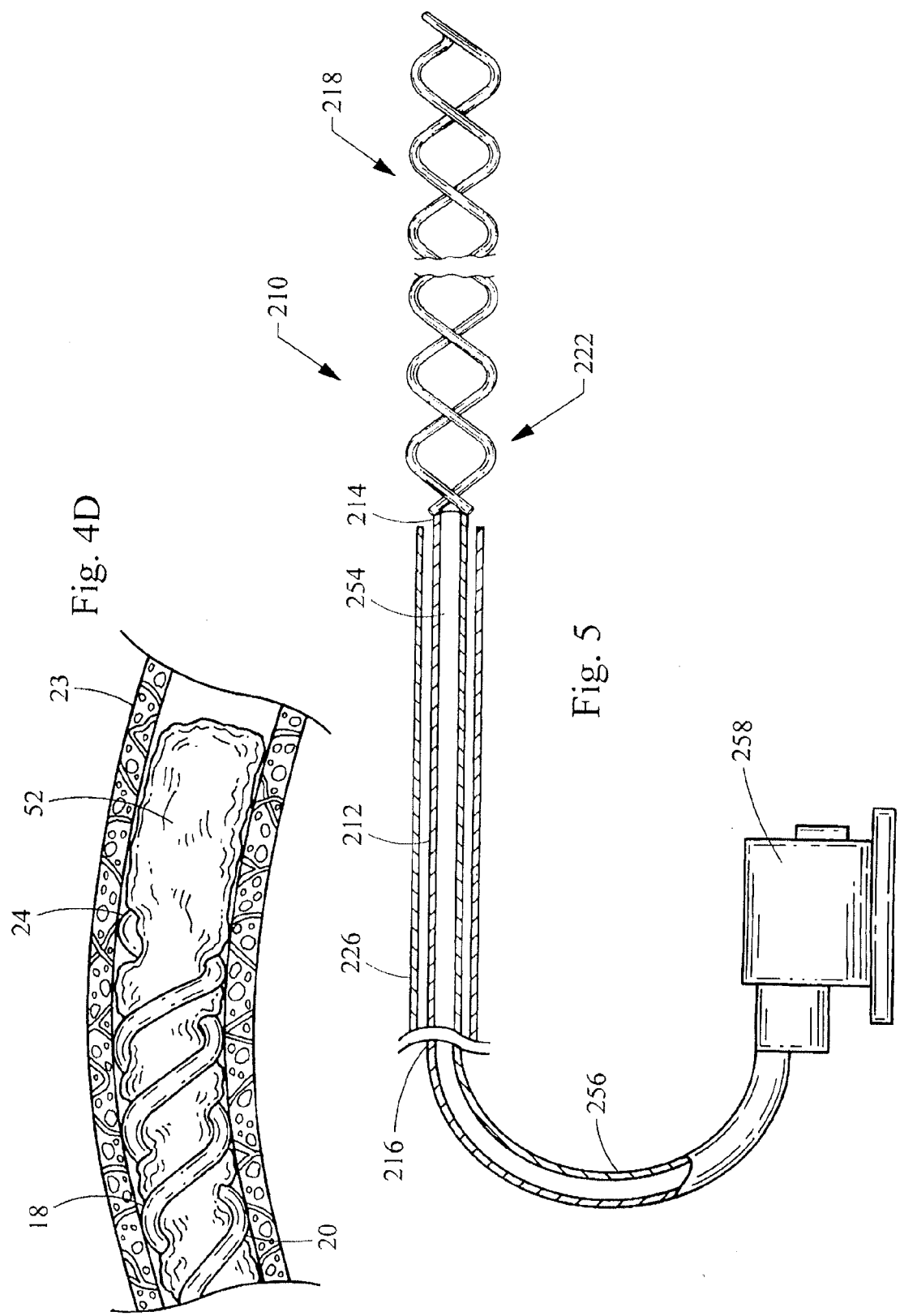

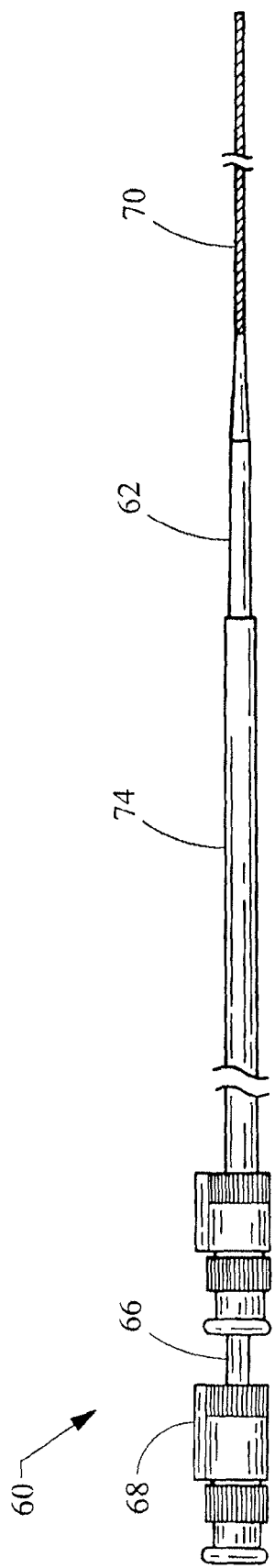
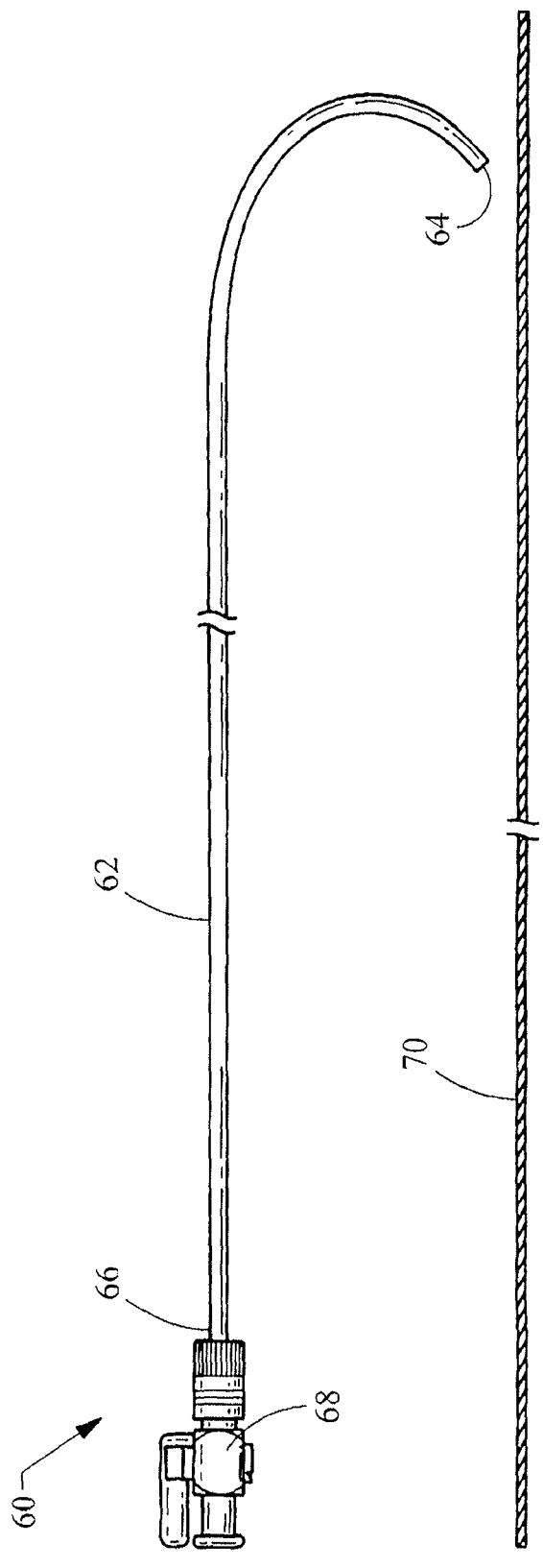
Fig. 6A
Fig. 6B

THROMBUS REMOVAL DEVICE

CROSS-REFERENCE TO RELATED APPLICATIONS

This patent application is a divisional of co-pending U.S. patent application Ser. No. 11/936,525, filed Nov. 7, 2007, which application claims the benefit of U.S. Provisional Application Ser. No. 60/857,760, filed on Nov. 8, 2006, entitled "THROMBUS REMOVAL DEVICE," the entire contents of which are incorporated herein by reference.

BACKGROUND

1. Field of the Invention

The present invention relates to medical devices. Specifically, the invention relates to a device for removing blood clots or thrombi from body vessels, such as the small arteries associated with the brain.

2. Description of Related Art

Mechanical thrombectomy is a procedure that has been in widespread use for many years. Typical thrombectomy devices are balloons that are inflated in a vessel and then withdrawn to pull clots into a sheath which can be withdrawn from the patient to remove the clots. Other devices are simple open ended catheters into which a clot is aspirated and removed from the patient. Another thrombectomy device employs a basket device that is opened within the clot so that the clot becomes captured in the basket. The basket can then be retrieved along with the clot. Still other devices use a small corkscrew shaped device that is collapsed inside a catheter. The catheter is passed through the clot, the corkscrew is pushed out of the catheter allowing the device to expand, capturing the clot for removal. Some corkscrew devices are simply "screwed" into the clot, then retracted into a catheter for removal before the corkscrew is retracted.

All of these devices may, however, have certain disadvantages. For example, the balloon catheter devices are first advanced through the clot before they can be inflated and retracted. The process of penetrating the clot with the balloon catheter device tends to push the clot deeper into the arterial circulation where it becomes even more difficult to remove. This issue also occurs with basket and corkscrew devices that are collapsed into an outer delivery sheath and passed through the clot before they can be deployed and retracted. The action of pushing a device through the center of the clot pushes the clot deeper into the artery and sometimes fragments the clot, making it into an even more dangerous embolus. The corkscrew devices that are screwed into the clot usually have a smooth rounded tip to prevent the corkscrew from penetrating the vessel wall or otherwise damaging the vessel wall as it is screwed into the clot. With these devices, however, the smooth, rounded central tip does not screw into the clot, but instead is pushed into the clot and then the remainder of the corkscrew is screwed into the clot. This results in a pushing force on the center of the clot and a pulling force on the periphery of the clot. These counter forces tend to macerate or fragment the clot and result in only a small part of the clot being captured. Some corkscrew devices may substitute a sharp tip that can screw directly into the clot for the rounded tip. However, sharp tips can penetrate the vessel wall just as easily as they can penetrate and capture the clot. Such devices are seldom used since they carry the very high risk of penetrating the vessel wall. When a bead or ball is applied to the tip of the device that is large enough to protect the vessel wall, it will be so large that it will tend to push the clot distally rather than penetrate the clot such that the clot can be captured and removed.

Another issue associated with conventional thrombectomy devices is that they are typically too large and too stiff for use in the small tortuous vessels of the brain. Also, many conventional devices use a central mandrel, wire, or some other structure for support. These support structures will also displace clots, making it difficult to capture all the clot material.

Still another issue includes capturing any of the loose fragments possibly dislodged from the clot during removal of the clot. Another issue arises if a thrombectomy device has a diameter smaller than the vessel diameter when deployed from the catheter. In such a case, some of the clot immediately adjacent the vessel wall may not be removed.

In view of the above, it is apparent that there exists a need for an improved mechanical thrombectomy device.

SUMMARY

The present invention provides a thrombus removal device that is small and flexible to, for example, capture clots in the cerebral vasculature. The distal tip of the device is configured as a loop to eliminate the danger of inadvertently penetrating through an artery wall while attempting to capture the clot.

In general, the device includes a shaft having a proximal end extending to a distal end attached to a helical coil. The helical coil has a closed configuration and an open configuration and is attached at a proximal end to the distal end of the shaft. The device also includes a sheath having a distal end and a proximal end and defining a lumen therein. As noted above, the helical coil includes a distal tip shaped as a loop and also has a plurality of spaced apart body portions. At least one body portion has an angle relative to a longitudinal axis extending through the helical coil. The angle of the at least one body portion is substantially the same as an angle of the loop relative to the longitudinal axis. The angle of the plurality of spaced apart body portions when the helical coil is in the open configuration is greater than the angle of the plurality of spaced apart body portions when in the closed configuration.

The helical coil includes a first outer diameter in the closed configuration and a second outer diameter in the open configuration. The first outer diameter is less than the second outer diameter according to a predetermined ratio. The helical coil is in the closed configuration when disposed within the lumen of the sheath and transitions to the open configuration when the sheath is retracted proximally from the distal tip of the helical coil. The helical coil further includes a closed length when in the closed configuration and an open length when in the open configuration. The closed length is greater than the open length according to a predetermined ratio.

In some embodiments, the shaft of the device defines a second lumen. The longitudinal axis of the helical coil is aligned with the second lumen. An aspiration device, such as a pump, may be attached to the proximal end of the shaft in fluid communication with the second lumen for aspirating loose thrombi into the second lumen. The pump may be manual, electrical or any other appropriate device.

The device may be made of shape memory alloy. The shape memory alloy may include nickel-titanium (Ni—Ti) alloys such as Nitinol.

In one embodiment, the shaft has a length of about 145 cm, and/or a diameter of about 0.014 inch, and/or the distal end of the shaft may be tapered. In those embodiments having the tapered distal end, a maximum diameter may be about 0.014 inch and a minimum diameter may be about 0.003 inch. The tapered distal end may be about 15 cm long.

In yet another embodiment, the helical coil may be made of wire. The wire is formed of a material selected from the group consisting of stainless steel, platinum, Nitinol, MP35N, and palladium. In some embodiments the wire may have a diameter of about 0.004 inch.

The outer diameter of the helical coil may be about 0.018 inch, and the length of the helical coil is in the range between about 2 and 10 cm. In a particular embodiment, the length of the helical coil is about 5 cm.

The present invention also includes a method for removing a thrombus from a body vessel. The method includes providing a thrombus removal device having a helical coil, in accordance with one of the devices described above, in the body vessel. The method also includes retracting a sheath proximally from a distal tip of the helical coil, expanding the helical coil into an open configuration, and rotating a shaft to screw the helical coil into the thrombus in the body vessel for capture of the thrombus.

The method may also include providing an aspiration device in fluid communication with a lumen of the shaft and aspirating loose thrombi while rotating the shaft to screw the helical coil into the thrombus. The loose thrombi may be aspirated into the lumen of the shaft by means of the aspiration device. In addition, the method may further include retracting the helical coil and the captured thrombus into a distal end of the sheath.

Further features and advantages will be apparent from the following description and from the claims.

BRIEF DESCRIPTION OF THE DRAWINGS

FIG. 1 is a perspective view of a thrombus removal device in a closed configuration within a sheath in accordance with one embodiment of the present invention;

FIG. 2 is the thrombus removal device of FIG. 1 in an open configuration;

FIG. 3a is a close-up view of one embodiment of a distal portion of the device of FIG. 2;

FIG. 3b is a close-up view of another embodiment of the distal portion of the device of FIG. 2;

FIG. 3c is a close-up view of one embodiment of the distal portion of the device of FIG. 1;

FIG. 4a is a close-up view of the distal portion of the thrombus removal device as it expands from the closed configuration to the open configuration;

FIG. 4b is a close-up view of the distal portion of the thrombus removal device of FIG. 2 just before engaging a thrombus;

FIG. 4c is a close-up view of the distal portion of the thrombus removal device of FIG. 2 after engaging the thrombus;

FIG. 4d is a close-up view of the distal portion of the thrombus removal device of FIG. 2 after engaging a long thrombus;

FIG. 5 is an alternate embodiment of the device shown in FIG. 2 including an aspiration device;

FIG. 6a is a side view of an assembly for deploying a thrombus removal device in accordance with one embodiment of the invention;

FIG. 6b is an exploded view of the assembly of FIG. 6a;

DETAILED DESCRIPTION

Figure 7:
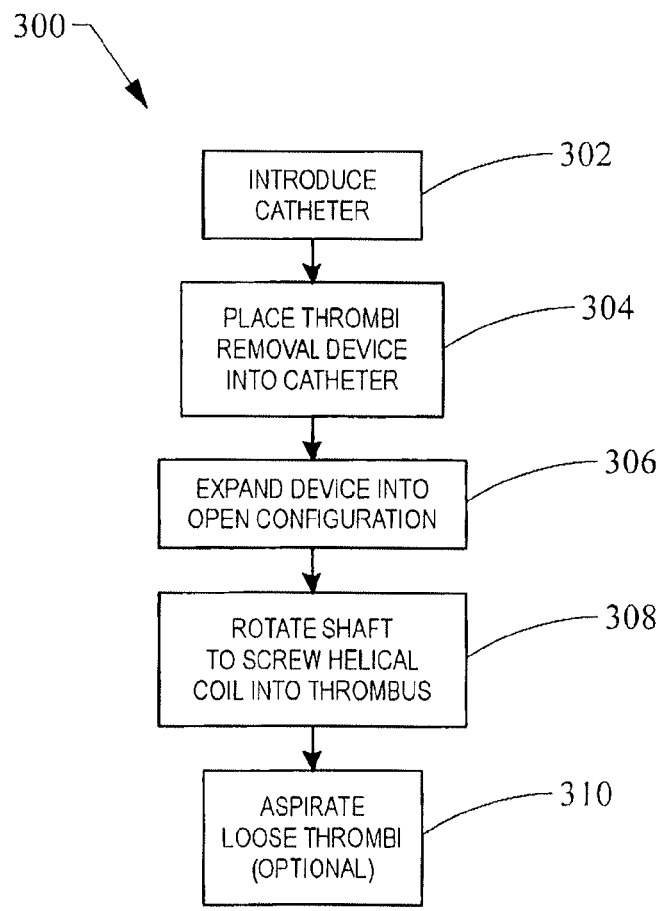
FIG. 7 is a flow chart of a sequence of steps for deploying a thrombus removal device in a body vessel.

Referring now to FIG. 1, a thrombus removal device embodying the principles of the present invention is illustrated therein and designated at 10. As its primary components the device 10 includes a shaft 12 having a proximal end 16 extending to a distal end 14 attached to a helical coil 18. The helical coil 18 has a distal portion 20 including a distal tip 24 and a proximal portion 22. A sheath 26 having a distal end 28 and a proximal end 30 defines a lumen 32 within which the shaft 12 and helical coil 18 are disposed. The device 10 is small and flexible to enable the helical coil 18 to penetrate a thrombus or clot without posing a danger of penetrating a body vessel wall (not shown).

The helical coil 18 is made of wire and in FIG. 1 is shown in a closed configuration 19, compressed inside the lumen 32 of the distal end 28 of the sheath 26. In the closed configuration 19, the helical coil 18 has a first outer diameter 34. When the sheath 26 is retracted proximally in FIG. 2 with respect to the distal tip 24, such that at least part of the helical coil 18 is no longer inside the lumen 32, the helical coil 18 expands and assumes an open configuration 21 having a second outer diameter 38.

In the closed configuration 19, the first outer diameter 34 is less than the second outer diameter 38 according to a predetermined compression ratio. The compression ratio may vary significantly between embodiments and is established based on a number of factors including, for example, a lumen inner diameter 36, the desired second outer diameter 38, and a wire diameter of the helical coil 18. In some embodiments, very little compression may be necessary, for example 5% or less. However, in other embodiments, significant compression may be desired, for example, on the order of 50% or more. In the embodiment shown in FIG. 1, the first outer diameter 34 is about 33% less than the second outer diameter 38 of FIG. 2. In other words, the second outer diameter 38 of FIG. 2 is one and one half times the first outer diameter 34.

In certain implementations, the wire of the helical coil 18 has a diameter of about 0.004 inch. However, in other embodiments, another diameter may be appropriate. The wire can be made from any suitable material, such as stainless steel, platinum, Nitinol, MP35N, and palladium.

FIGS. 3a and 3b show a close-up view of the helical coil 18 outside of the sheath 26 in the open configuration 21. As best shown in FIG. 3a, the wire is initially coiled into a helical spring. The helical coil is folded or doubled back on itself and then twisted together into a two-filar helical coil with a plurality of body portions 40. An open longitudinal spacing ($d_1$) and an open lateral spacing ($d_2$) between the individual winds or turns 42 of the coil are selected so that the helical coil 18 screws into the clot while providing ample open area for secure clot capture. The proximal portion 22 of the helical coil 18 terminates with two ends 44. The distal portion 20 near the distal tip 24 is shaped as a small loop formed when the coil is folded or doubled back through about 180°. The overall diameter of the two-filar helical coil 18 is about the same size as the unfolded spring, for example, approximately 0.018 inch.

The length of the helical coil 18 may be any length appropriate for a particular application. The length may, for example, be in the range between about 2 and 10 cm. In the embodiment shown, the helical coil 18 is approximately 5 cm long. An outer diameter of the helical coil 18 be any diameter appropriate for a particular application. For example, the outer diameter may be approximately 0.018 inch while in other applications it may be 0.014 inch and smaller. In other examples, the outer diameter may be larger than 0.018 inch. In any case, the outer diameter should be selected to at least accommodate both the size of the thrombi to be removed and the size of the body vessel in which it is to be used.

The loop at the distal tip 24 is a single loop with a first open angle ($\alpha_1$) relative to a longitudinal axis (A) that is the same or about the same as a second open angle ($\alpha_2$) of a body portion 40 that extends away from the loop as it extends from the bottom to the top of the distal portion 20 as illustrated in FIG. 3a. When the loop is formed at the distal tip 24, an adjacent first bend 46 and a second bend 48 are also formed. In one embodiment, as shown in FIG. 3a, the first bend 46 may be aligned approximately with or tangent to the longitudinal axis (A).

An alternative embodiment is shown in FIG. 3b and includes features equivalent to FIG. 3a, for example, a helical coil 118 is equivalent to the helical coil 18, a body portion 140 is equivalent to the body portion 40, and a longitudinal axis (AA) is equivalent to the longitudinal axis (A). However, in the embodiment of FIG. 3b a first bend 146 may be configured in non-alignment relative to the longitudinal axis (AA). As shown, the first bend 146 has a turn or bend that is not tangent or is not in alignment with axis (AA). In yet another example (not shown), the first bend 146 may be aligned with the second bend 148.

In either of the embodiments, the loop screws into the clot without applying a pushing force parallel to a longitudinal axis of a vessel so that the clot is not pushed in the distal direction. Additionally, the loop protects the vessel wall by preventing the helical coil 18 from corkscrewing and penetrating into the vessel wall while enabling the helical coil to corkscrew and penetrate into a clot in order to capture the clot.

Turning now to FIG. 3c, the helical coil 18 is shown in the closed configuration 19 inside the sheath 26 such that the distal tip 24 is fully contained within the distal end 28 of the sheath 26. In this configuration, an interior wall 33 of the lumen 32 compresses the helical coil 18 such that it assumes the first outer diameter 34. Thus, a closed lateral spacing ($d_4$) is less than the open lateral spacing ($d_2$) and a closed longitudinal spacing ($d_3$) is greater than the open longitudinal spacing ($d_1$). Additionally, a first closed angle ($\beta_1$) of the distal tip 24 in the closed configuration 19 is less than the first open angle ($\alpha_1$) of the distal tip 24 of the open configuration 21. The same holds true for a second closed angle ($\beta_2$) of the body portions 40 compared to the second open angle ($\alpha_2$).

The change in length and angle is proportional to the change in diameter described above. For example, a reduction in diameter of 33% may result in the closed longitudinal spacing ($d_3$) being about 50% greater than the open longitudinal spacing ($d_1$). Similarly, the same 50% reduction in diameter may cause a second closed angle ($\beta_2$) to be about 38% smaller than the second open angle ($\alpha_2$). It is important to note that the above proportions are merely examples. Different proportions are possible depending on the exact requirements and geometry of each application.

The loop at the distal tip 24 can be filled or coated, or otherwise include a highly radiopaque material such as, for example, gold, silver, platinum, copper, tungsten, cobalt, palladium, or another appropriate material to make the distal tip 24 of the helical coil 18 visible under fluoroscopy. The helical coil 18 itself can be made of platinum wire for added radiopacity. Rather than using a wire, the helical coil 18 can be laser cut from a tube, and then the loop is bent into the tip into the correct angle and position.

The shaft 12 is preferably made of a material that transmits rotation or torque around curves in the vasculature. Shape memory alloys are well suited to this application because they have the desirable property of becoming rigid when heated above a transition temperature. A shape memory alloy suitable for the present invention is Ni—Ti available under the more commonly known name Nitinol. When this material is heated above the transition temperature, the material undergoes a phase transformation from martensite to austenite, such that the material becomes rigid. The transition temperature is dependent on the relative proportions of the alloying elements nickel (Ni) and titanium (Ti) and the optional inclusion of alloying additives. Often the proportions of Ni and Ti are selected so that the material is austenite at body temperature.

Returning to FIG. 2, the proximal portion 22 of the helical coil 18 is attached to the distal end 14 of the shaft 12 by any suitable attachment means, for example, glue, solder or welding. The distal end 14 of the shaft 12 may taper to a shaft tip 15 so that there is a gradual transition from the stiff portion of the shaft 12 to the helical coil 18. The tapered portion can be any length and can have any suitable combination of decreasing diameters. In some implementations, the shaft is made of Nitinol wire with a diameter of about 0.014 inch and is about 145 cm long. The distal end 14 may, for example, taper from the diameter of about 0.014 inch to about 0.003 inch at the tip 15 over a length of about 15 cm. The shaft 12 may be provided with a pin vise or any other suitable handle device to facilitate rotation of the shaft 12 and the helical coil 18.

It is important to note that although these dimensions and this description relate to a device sized to work in the cerebral arteries, the device can be dimensioned to work in any size artery or anatomy for thrombectomy, embolectomy or crossing completely stenosed or nearly completely stenosed areas within any body vessels.

Referring now to FIGS. 4a-4d, the operation of the helical coil 18 of the device 10 is shown within a body vessel 23. Turning first to FIG. 4a, the helical coil 18 is shown in transition between the closed configuration 19 and the open configuration 21 as the sheath 26 is retracted proximally. As can be seen, each body portion 40 sequentially expands from the closed to the open configuration as the distal end 28 of the sheath 26 is retracted proximally away from the distal tip 24.

Once the helical coil 18 has expanded into the open configuration 21, the distal tip 24 of the helical coil 18 is positioned within closed proximity to a clot or thrombus 50 as shown in FIG. 4b. Next, the physician rotates the shaft 12 so that the helical coil 18 screws into the thrombus 50. In FIG. 4c, the helical coil 18 is shown screwed into the thrombus 50, capturing the thrombus 50 in the distal portion 20 of the helical coil 18. Next, the helical coil 18 and the thrombus 50 are removed by retracting the coil and clot into the sheath 26 by the physician pulling proximally on the shaft 12.

The device 10 is capable of removing clots of differing lengths such as, for example, a long thrombus 52 shown in FIG. 4d. In this case, the long thrombus 52 may be captured since the helical coil 18 may be configured to be longer than the long thrombus 52. As a result, the device 10 may capture either the thrombus 50 (see FIG. 4c), the long thrombus 52 (see FIG. 4d), or a clot having same other length. Thus, the device 10 has features that make it well suited for the very small vessels that are encountered in the brain which may have clots of differing lengths.

Alternative embodiments, such as the one shown in FIG. 5, provide a device 210 configured to aspirate loose thrombi or portions of clots that may come loose while being captured by a helical coil 218. This embodiment includes features equivalent to the device 10 shown in FIG. 2. For example, the helical coil 218 is equivalent to the helical coil 18, and a sheath 226 is equivalent to the sheath 26. In FIG. 5, a shaft 212 has a distal end 214 and further includes a second lumen 254. The distal end 214 is attached to a proximal portion 222 of the helical coil 218 such that the helical coil 218 is aligned approximately coaxial with the second lumen 254. A proximal end 216 of the shaft 212 is attached, for example, to a flexible tube 256, placing the second lumen 254 into fluid communication with an aspiration device 258. The aspiration device 258 may include, for example, a manual pump, an electric pump, or other similar devices. Activating the aspiration device while screwing into a clot or thrombus provides additional effectiveness in capturing the thrombus by aspirating any loose clot particles or thrombi into the second lumen 254. In this embodiment, the shaft 212 may be made from any of the materials described above for the shaft 12, or it may include a catheter made of a suitable polymer having an appropriate blend of stiffness and flexibility such as, for example, polyimide (PI), nylon or other similar polymers.

The thrombus removal device 10 may be used independently without any other delivery system or mechanism. Alternatively, the device 10 may be used, for example, with an assembly 60 as depicted in FIGS. 6a and 6b. As shown, the assembly 60 includes an outer catheter 62 (equivalent to the sheath 26) having a distal end 64 through which the device 10 is positioned for deployment in a body vessel. The outer catheter 62 is preferably made of a soft, flexible material such as silicon or another suitable material. Generally, the outer catheter 62 also has a proximal end 66 and a plastic adaptor or hub 68 to receive the thrombus removal device 10. The size of the inner catheter 62 may be based, for example, on the size of the body vessel into which the inner catheter 62 is to be inserted and a first outer diameter of the helical coil.

The assembly 60 may also include a wire guide 70 configured to be percutaneously inserted within the vasculature to guide the inner catheter 62 to a location adjacent the clot or thrombus. Alternatively, the thrombus removal device 10 may be employed as a wire guide. The device 10 is placed in the outer catheter 62 prior to treatment of the thrombus. The device is then guided through the outer catheter 62 from the hub 68 and distally beyond the distal end 64 of the outer catheter 62 to a location within the vasculature near the thrombus or clot.

The assembly 60 may include a polytetrafluoroethylene (PTFE) introducer sheath 74 for percutaneously introducing the wire guide 70 and the outer catheter 62 into a body vessel. Of course, any other suitable material may be used for the introducer sheath 74. The introducer sheath 74 may have any suitable size, for example, between about three-french and eight-french. The introducer sheath 74 facilitates inserting the outer catheter 62 percutaneously to a desired location in the body vessel and provides stability to the outer catheter 62 at the desired location in the body vessel. For example, as the introducer sheath 74 is held stationary within the body vessel it adds stability to the outer catheter 62 as the outer catheter 62 is advanced through the introducer sheath 74 to the desired location in the vasculature.

When the distal end 64 of the outer catheter 62 is at the location near the thrombus the guide wire 70 is removed, if necessary, and the thrombus removal device 10 is inserted into the outer catheter 62 and is advanced coaxially through the outer catheter 62 for deployment through the distal end 64 of the outer catheter 62. In this configuration, a proximal end of the shaft can be used to mechanically advance or push the thrombus removal device 10 through the outer catheter 62.

Turning now to FIG. 7, there is shown one example of a sequence of steps of a process 300 for removing thrombi from a body vessel when employing the assembly 60 and the thrombus removal device 10 or 210. For clarity, only the reference numbers associated with the removal device 210 shown in FIG. 5 will be used in describing this process.

In step 302, the process 300 includes a physician percutaneously introducing the outer catheter 62 into the body vessel. The physician may use any suitable means, for example, fluoroscopy, to verify the placement of outer catheter 62. In step 304, the thrombus removal device 210 is placed into the outer catheter 62 in a closed configuration. At step 306 the removal device 210 is expanded into an open configuration by retracting the distal end 64 of the outer catheter 62 from a distal tip of the removal device 210. In step 308, the physician rotates the shaft 212 to screw the helical coil 218 into the thrombus until the thrombus is captured within the helical coil 218. Optionally, in step 310 the physician may also aspirate any thrombi that come loose when the helical coil 218 is screwed into the thrombus. After capturing the thrombus, the physician may advance the device 210 further in the distal direction toward additional thrombi that may reside in the vessel and then repeat the above procedure to capture the additional thrombi.

Figure 8:
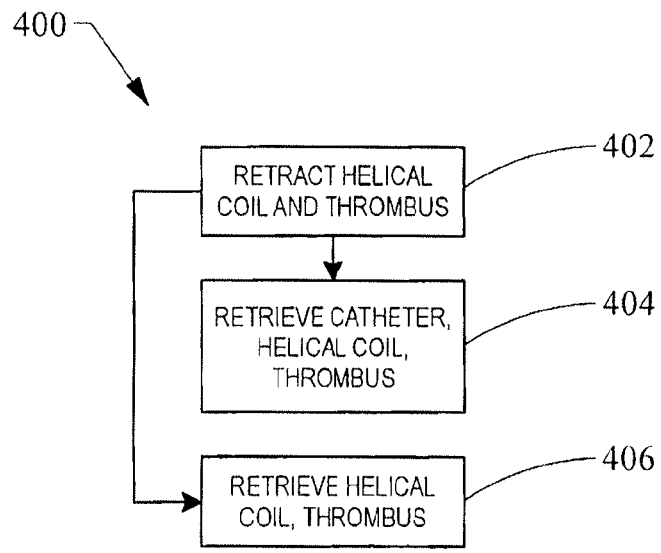
FIG. 8 is a flow chart of a sequence of steps for retrieving a thrombus captured by a thrombus removal device.

In yet another example of the present invention, FIG. 8 depicts a process 400 for retrieving the thrombus removal device after it has captured a thrombus or thrombi. As above, only the reference numbers associated with the removal device 210 will be used in describing this process. In step 402, the physician pulls on a proximal end of the shaft 212 to retract the helical coil 218 and the captured thrombus into the outer catheter 62. In step 404 the outer catheter 62, the thrombus removal device 210, and any captured thrombi are retrieved from the body vessel. Alternatively, the outer catheter 62 may not be removed from the body vessel. Instead, the thrombus removal device 210 and any captured thrombi are retrieved from the patient's body by pulling the device 210 out of the outer catheter 62 in optional step 406. After the helical coil 218 is cleansed of any thrombi, the device 210 can be reinserted into the outer catheter 62 to capture additional thrombi, or another device may be inserted into the outer catheter 62 to perform another procedure.

As a person skilled in the art will readily appreciate, the above description is meant as an illustration implementing the principles of this invention. This description is not intended to limit the scope or application of this invention in that the invention is susceptible to modification, variation and change without departing from the spirit of this invention as defined in the following claims.

We claim:

1. A method for removing thrombi from a body vessel, the method comprising:

providing a thrombus removal device in the body vessel, the device including
a shaft including a distal end and a proximal end and having a first lumen formed therethrough;
a sheath including a distal end and a proximal end and having a second lumen therethrough;
a helical coil having a closed configuration and an open configuration and including a proximal portion extending to a distal portion terminating in a distal tip, the proximal portion being attached to the distal end of the shaft, the distal tip being shaped as a loop, the helical coil further including a plurality of spaced apart body portions, at least one body portion having an angle relative to a longitudinal axis extending through the helical coil, the angle being substantially the same as an angle at which the distal tip is oriented relative to the longitudinal axis such that the distal tip is spaced away from the longitudinal axis by a first bend and a second bend adjacent the loop, the closed configuration of the helical coil having a first outer diameter and the open configuration having a second outer diameter, the first outer diameter being less than the second outer diameter, the helical coil being in the closed configuration when disposed inside the second lumen of the sheath and being in the open configuration when disposed outside of the second lumen of the sheath, wherein the helical coil forms a double helix;

retracting the sheath proximally from the distal tip of the helical coil;

expanding the helical coil to the open configuration; and rotating the shaft to screw the helical coil into a thrombus residing in the body vessel for capture of the thrombus.

2. The method of claim 1, wherein the step of rotating includes aspirating thrombi.

3. The method of claim 2, wherein the thrombi are aspirated into the first lumen formed through the shaft.

4. The method of claim 3, further comprising providing an aspiration device in fluid communication with the first lumen of the shaft; and retracting the helical coil and the captured thrombus into the sheath.

* * * * *